United States Patent [19]

Foltz

[11] Patent Number: 4,998,562
[45] Date of Patent: Mar. 12, 1991

[54] FLOW CONTROL VALVE
[75] Inventor: Carl L. Foltz, Clearwater, Fla.
[73] Assignee: Halkey-Roberts Corporation, St. Petersburg, Fla.
[21] Appl. No.: 191,701
[22] Filed: May 9, 1988

Related U.S. Application Data

[63] Continuation-in-part of Ser. No. 867,238, May 23, 1986, Pat. No. 4,744,391.

[51] Int. Cl.$^5$ .............................................. F16K 31/50
[52] U.S. Cl. ................................. 137/877; 128/685; 137/886; 251/121; 251/215
[58] Field of Search ................ 128/685; 137/877, 886; 251/121, 122, 205, 215

[56] References Cited
U.S. PATENT DOCUMENTS

| 2,621,011 | 12/1952 | Smith .................................. 251/121 |
| 2,685,294 | 8/1954 | Gold et al. ........................ 251/122 X |
| 3,255,775 | 6/1966 | Albro et al. ..................... 251/215 X |
| 3,747,894 | 7/1973 | Pepper ............................... 251/215 |
| 3,954,099 | 5/1976 | Raczkowski et al. ........... 251/122 X |
| 4,610,424 | 9/1986 | Koppers et al. ..................... 251/121 |
| 4,744,391 | 5/1988 | Lardner ........................... 137/886 X |
| 4,752,031 | 6/1988 | Merrick ............................ 251/216 X |

FOREIGN PATENT DOCUMENTS

| 1550555 | 11/1969 | Fed. Rep. of Germany ...... 251/121 |
| 2758894 | 8/1978 | Fed. Rep. of Germany ...... 128/685 |

Primary Examiner—Gerald A. Michalsky
Attorney, Agent, or Firm—Dominik, Stein, Saccocio, Reese, Colitz & Van Der Wall

[57] ABSTRACT

A flow control valve to regulate the bleed flow rate of a pressurized vessel at one of only two available bleed flow rates. The flow control valve comprises an axial main gas flow passageway with an integral check valve that allows pressurization of the vessel, a bleed passageway for depressurization of the vessel, and a threaded bleed passageway cap that allows bleeding of the vessel at one of only two rates available, based on the counter-rotated position of the bleed cap.

7 Claims, 2 Drawing Sheets

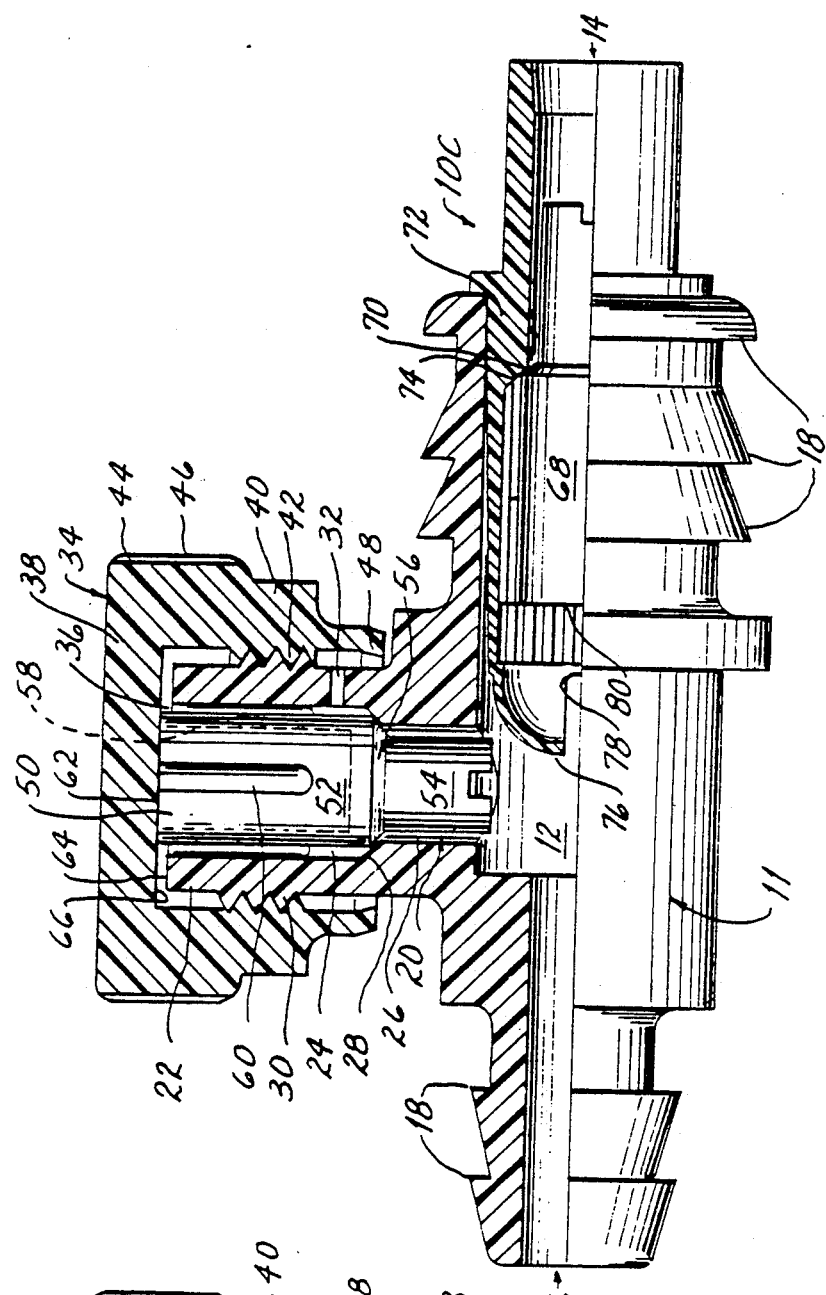

મ4,998,562

FLOW CONTROL VALVE

CROSS REFERENCE TO RELATED APPLICATIONS

This application is a continuation-in-part of patent application, Ser. No. 867,238, filed May 23, 1986, now U.S. Pat. 4,744,391.

BACKGROUND OF THE INVENTION

1. Field of the Invention

This invention relates to flow control valves operable to bleed pressure from a pressurized source. More particularly, this invention relates to flow control bleed valves having a check valve incorporated therein allowing pressurization of the pressure source.

2. Description of the Background Art

Presently, there exist many types of flow control valves operable to regulate the flow of a fluid into and out of a tank or other container. Basically, the more predominate type of flow control valve comprises a spring-loaded ball which is urged against a valve seat by means of a vented turn knob. During operation, rotation of the turn knob increases (or decreases) the space between the ball and the valve seat, thereby regulating the flow of fluid therethrough. These types of flow control valves work quite suitably and reliably. However, since each component part of the flow control valve requires machining and deburring, these valves are manufactured at a relatively high cost.

In many applications, it is desirable to incorporate a check valve into the flow control valve such that the flow of fluid in one direction is uninhibited, while the flow of fluid in the opposite direction is controlled. For example, in the medical field, it is almost universal practice to utilize a flow control/check valve in-line between the pump bulb and the inflatable cuff of a blood pressure monitor (sphygmomanometer). The check valve of a control valve of this nature allows the inflatable cuff to be freely inflated to a desired pressure by pumping of the pump bulb. After the cuff is suitably inflated to the desired constricting pressure about the patient's arm, the cuff is slowly deflated by slowly bleeding the pressure contained therein through the use of the flow control valve. Of course, many other applications exist which require the use of a flow control valve having a check valve incorporated therein.

In regard to sphygmomanometers, there exists a need for a flow control valve having a preset bleed rate which allows the inflatable cuff to be bled at a preset, constant rate so that the inflatable cuff is not deflated too rapidly. The operator thus obtains an accurate systolic and diastolic pressure reading.

Therefore, it is an object of this invention to provide an apparatus which overcomes the aforementioned inadequacies of the prior art devices and provides an improvement which is a significant contribution to the advancement of the flow control valve art.

Another object of this invention is to provide a flow control valve which is economical to manufacture and highly reliable in operation.

Another object of this invention is to provide a flow control valve composed of injection molded parts which do not require machining or deburring prior to assembly thereby reducing the cost of manufacture thereof.

Another object of this invention is to provide a flow control valve having a turn knob which, on rotation, variably controls the flow of fluid therethrough.

Another object of this invention is to provide a flow control valve having a check valve incorporated therein, allowing a tank or other container to be inflated to a pressurized state by means of the check valve and then slowly deflated to a depressurized state by means of the variable flow control valve.

Another object of this invention is to provide a flow control valve operable as a bleed valve to bleed pressure from a pressurized source.

Another object of this invention is to provide a flow control valve having a turn knob, which, on rotation, controls the flow of fluid therethrough at a preset rate allowing the flow control valve to be utilized in conjunction with a sphygmomanometer to obtain systolic and diastolic pressure readings.

Another object of this invention is to provide a flow control valve having a turn knob which, upon rotation by approximately a quarter turn, controls the flow of fluid therethrough at a first preset rate, and then, upon further rotation of the turn knob, controls the flow of fluid therethrough at a second, higher rate.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention comprises a flow control valve for variably controlling the flow of a fluid therethrough. The invention further comprises a check valve incorporated within the flow control valve. The flow control valve having a check valve incorporated therein allows the valve to be used for inflating a tank or other container, such as a blood pressure cuff, to a pressurized state, with the check valve thereof functioning to maintain the pressure within the tank during pressurization and thereafter. The pressurized container may then be depressurized by bleeding the fluid therefrom upon variably opening the flow control valve from a closed position.

More particularly, the flow control valve of the invention comprises an integral body having a main axial fluid passageway with an input and an output. A check valve is positioned within the main fluid passageway allowing a fluid such as air, to flow from the input to the output while preventing the flow of air from the output to the input. The check valve may comprise a conventional check valve having a valve element freely reciprocatingly positioned therein which seats against a valve seat to prevent the flow of air from the output to the input. Alternatively, the check valve may comprise a check valve having a preset cracking pressure such as the check valve disclosed in U.S. Pat. No. 3,831,629, U.S. Pat. No. 4,602,655 or in U.S. Pat. No. 4,681,132 entitled "Check Valve with Preset Cracking Pressure" filed May 23, 1986, the disclosure of each of which is hereby incorporated by reference herein. The flow control valve further comprises a bleeder valve positioned within a bleeder passageway connected in fluid communication with the main fluid passageway and operable by means of a turn knob or cap. During use, upon rotation of the turn knob from a closed to a variably open position, the pressure contained within the tank is variably bled to the atmosphere via a vent hole.

In an improved embodiment of the invention, the bleed valve of the flow control valve comprises a cylindrical valve element having a distal end which concentrically seats into a cylindrical recess formed in the bottom of the bleed fluid passageway. The diameter of the distal end of the valve element is dimensioned relative to the recess such that when the valve element is unseated from the bottom surface of the recess, only a small annular passageway exists between the distal end and the inner wall of the recess. Thus, bleeding at a preset rate occurs. Further movement of the distal end of the bleed element away from the recess causes the distal end to move out of the recess altogether allowing the bleeding at a second, higher rate.

It is noted that the improved embodiment of the flow control valve is particularly adapted to be used in conjunction with a sphygmomanometer. Specifically, the flow control valve controls precise bleeding of the sphygmomanometer inflation cuff allowing the operator, such as a nurse, to obtain accurate systolic and diastolic pressure readings. Once such pressure readings are obtained, the inflatable cuff may be quickly deflated once the turn knob is further rotated to move the distal end of the valve element out of the recess in the bleed passageway. Thus, repeated attempts to obtain accurate systolic and diastolic pressure readings are substantially eliminated.

All of the components of the flow control valve of the invention are manufactured from injection molding techniques and then simply assembled together by hand or by automatic assembly machines. The machining and deburring typically required by prior art flow control valves are eliminated. Thus, the flow control valve of the invention may be economically manufactured and assembled at significant cost savings when compared with prior art flow control valves.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a partial cross-sectional view of the flow control valve of the invention;

FIG. 2 is a left end view of the flow control valve of the invention of FIG. 1.

Similar reference characters refer to similar parts throughout the several views of the drawings.

DETAILED DESCRIPTION OF THE PREFERRED EMBODIMENT

Figure 3:
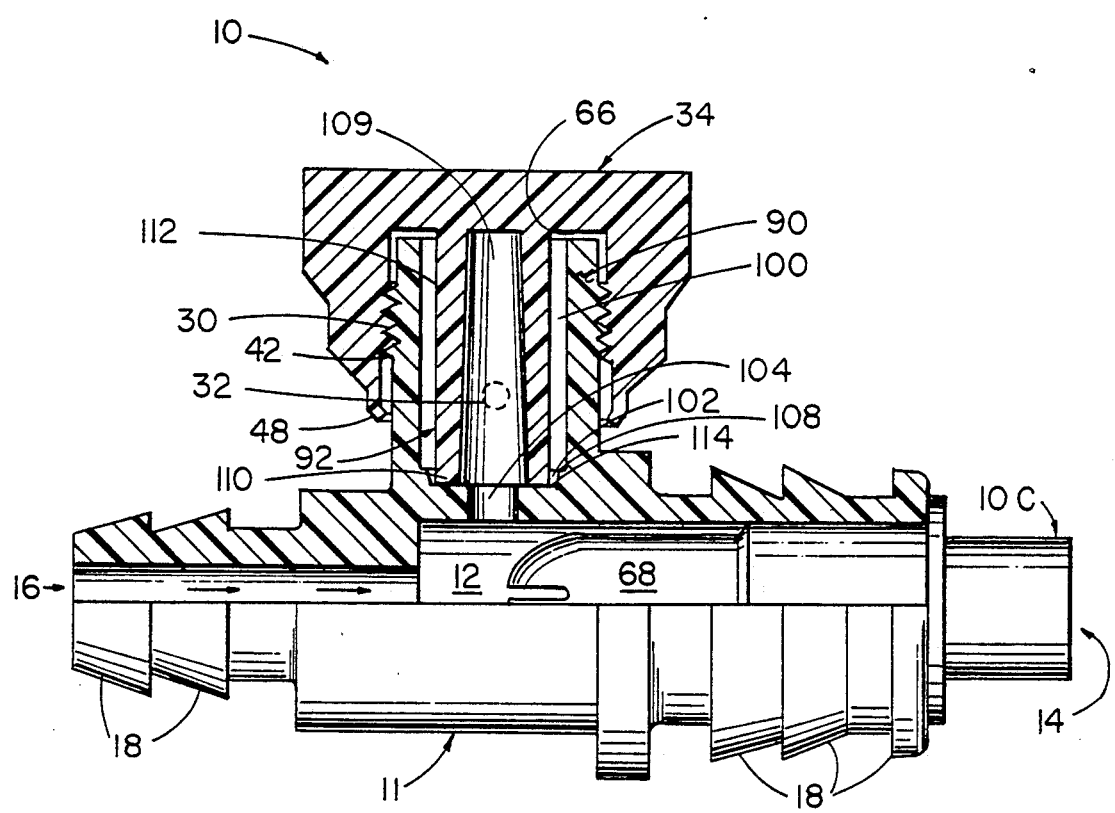
FIG. 3 is a partial cross-sectional view of the new embodiment of the flow control valve of the invention.

The flow control valve 10 of the invention comprises a bleed valve 10B and a check valve 10C. More particularly, valve 10 comprises an integral body 11 having main axial fluid passageway 12 with input 14 and output 16. As shown in FIG. 2, the main fluid passageway 12 preferably comprises a generally cylindrical configuration. A plurality of inwardly disposed barbs 18 are annularly positioned about the outside surface of the input 14 and output 16 of the main fluid passageway 12 to facilitate connection of a plastic tube to the input 14 and the output 16.

The body 11 of the flow control valve 10 further comprises a bleed fluid passageway 20 connected in fluid communication with the main fluid passageway 12. The cylindrical wall 22 of the bleed fluid passageway 20 comprises a large diameter portion 24 and a small diameter portion 26 joined together by means of a forwardly converging frustro-conical valve seat 28. The exterior surface of wall 22 of the bleed fluid passageway 20 comprises exterior threads 30. Finally, bleed hole 32 is formed through the large diameter portion 24 of wall 22 of the bleed fluid passageway 20.

Bleed knob or cap 34 is provided for threaded engagement over the opened end 36 of the large diameter portion 24 of the bleed fluid passageway 20. More particularly, bleed cap 34 comprises a generally circular configuration having a base portion 38 and annular wall portion 40. An internal thread 42 is formed along the lumen of the annular wall portion 40 for threaded engagement with the thread 30 of wall 22 of the bleed fluid passageway 20. The outside annular surface 44 of the bleed cap 34 may be provided with a plurality of knurled ridges 46 or the like to enhance gripping of the bleed cap 34 during use. Further, the annular wall portion 40 may include an inwardly crimped annular edge 48 to prevent the bleed cap 34 from being inadvertently completely unthreaded from the bleed fluid passageway 20 during use.

A bleed valve element or poppet 50 is reciprocatingly positioned within the bleed fluid passageway 20. The valve element 50 comprises a large diameter portion 52 and a small diameter portion 54 joined together by a forwardly converging frustro-conical valve seat 56 corresponding to the large diameter portion 24, small diameter portion 26 and valve seat 28 of the bleed fluid passageway 20. Hence, the valve element 50 is loosely positioned within the bleed fluid passageway 20 with the respective seats 28 and 56 sealingly engaging each other to form a fluid-tight seal between the seats 28 and 56 when the seat 56 of the element 50 is forced against the seat 28 of the bleed fluid passageway 20. Finally, the large diameter portion 52 of the valve element 50 preferably comprises a forwardly formed blind axial cylindrical hole 58 along the length thereof. A plurality of axially extending lands or ribs 60 are positioned exteriorly along the outside surface of the large diameter portion 52 of the valve element 50 to centrally locate the valve element 50 within the bleed fluid passageway 20.

The longitudinal length of the large diameter portion 52 is appreciably greater than the longitudinal length of the large diameter portion 24 of the bleed fluid passageway 20 such that the rearward edge 62 of the valve element 50 appreciably protrudes from the rearward edge 64 of the bleed fluid passageway 20 and is engagable by the inward surface 66 of the base portion 38 of the bleed cap 34. Consequently, it should be readily apparent that clockwise rotation of the bleed cap 34 increasingly causes its inward surface 66 to engage against the rearward edge 62 of the valve element 50, thereby increasingly forcing the valve element 50 into the bleed fluid passageway 20 and, in turn, increasingly forcing the seat 56 of the valve element 50 against the seat 28 of the bleed fluid passageway 20. It is noted that, as the seat 56 of the valve element 50 is increasingly forced against the seat 28 of the bleed fluid passageway 20, the sleeve formed by the hole 58 within the large diameter portion 52 of the element 50 increasingly flexes to a "wavy" configuration proportional to the amount of force exerted on the element 50 by the bleed cap 34. This function correspondingly increases the amount of sealing force present between the mated seats 56 and 28 until the bleed cap 34 is fully threaded onto the bleed fluid passageway 20. Moreover, it is noted that due to the flexing of the large diameter portion 52 of the element 50, the bleed cap 34 may be fully threaded onto the bleed fluid passageway 20 without damaging the mated seats 56 and 28.

During bleeding, the bleed cap 34 may be counterrotated to reduce the sealing force between the mated seats 56 and 28 until the fluid begins to escape between the seats 56 and 28 and exits the valve 10 via bleed hole 32. Obviously, as the bleed cap 34 is increasingly unthreaded from the bleed fluid passageway 20, more bleeding will occur at an increased rate until the tank or other container is depressurized or until the bleed cap 34 is threaded onto the bleed fluid passageway 20 to reduce or completely stop bleeding.

Returning now to the check valve 10C of the flow control valve 10, the check valve 10C may comprise the check valve illustrated in U.S. Pat. No. 3,831,629, in U.S. Pat. application, Ser. No. 450,453 filed Dec. 16, 1982, now U.S. Pat. No. 4,602,655, or in U.S. Pat. application, entitled "Check Valve with Preset Cracking Pressure", Ser. No. 867,319, filed May 23, 1986, now U.S. Pat. No. 4,681,132, the disclosures of which are hereby incorporated by reference herein. Briefly summarizing the first two such disclosures, the check valve 10C of that type comprises a valve element 68 having a forwardly converging frustro-conical seat 70 positioned within a housing 72 correspondingly having a forwardly converging frustro-conical seat 74. The rearward end 76 of the housing 72 is folded inwardly at crimp 78 to compressibly engage rearward edge 80 of the valve element 68 thereby forcibly engaging the seats 70 and 74 together to form an airtight seal capable of being opened at a predetermined cracking pressure exerted on the input of the check valve 10C either by fluid pressure or by a syringe or other instrument.

Alternatively, however, check valve 10C may comprise a check valve having no cracking pressure in which the valve element 68 is loosely reciprocatingly positioned within the housing 72 such that the rearward crimp 78 reciprocatingly retains the valve element 68 within housing 72 but does not exert a compressive force on the valve element 68 (see FIG. 1).

FIG. 3 illustrates the new embodiment of the flow control valve 10 of the invention having a newly designed bleed fluid passageway 90 and a newly designed bleed valve element 92.

More particularly, refering to FIG. 3, the bleed fluid passageway 90 of the new embodiment of the invention comprises a generally cylindrical lumen 100 having a generally cylindrical recess 102 concentrially formed in the bottommost portion 108 of the bleed fluid passageway 90. An axial hole 104 extends through the bottommost portion 108 of the bleed fluid passageway 90 into the main fluid passageway 12. Preferably, axial hole 104 is concentrically positioned relative to recess 102.

The new embodiment of the bleed valve element 92 is preferably substantially cylindrical and integrally formed with the bleed cap 34 to concentrically extend from its inward surface 66. The bleed valve element 92 includes a blind hole 109 extending from the distal end 110 of the bleed valve element 92 to an area approximate the bleed cap 34. Thus, it is noted that the bleed valve element 92 preferably comprises a substantialy cylindrical wall 112 having its distal end 110 transversely formed.

The outer diameter of the distal end 110 of the cylindrical wall 112 of the bleed valve element 92 includes a diameter smaller than the inner diameter of cylindrical recess 102 allowing the distal end 110 to concentrically engage therein and seat against the bottom surface 114 of the recess 102. The length of the bleed valve element 92 is appreciably greater than the length of the bleed fluid passageway 20 such that the distal end 110 of the bleed valve element 92 may be seated against the bottom surface 114 by rotation of the bleed cap 34.

During use, clockwise rotation of the bleed cap 34 sealingly seats the distal end 110 of the bleed valve element 92 against the bottom surface 114 of the recess 102 about hole 104 of the bleed fluid passageway 90. Bleeding through the bleed fluid passageway 90 is therefore prevented.

To begin bleeding, counter rotation of the bleed cap 34 causes the distal end 110 of the bleed valve element 92 to become unseated from the bottom surface 114 of the recess 102 of the bleed fluid passageway 90. The rate of bleed is controlled by the cross-sectional area between the distal end 110 of the cylindrical wall 112 and the inner wall of recess 102.

Further counterrotation of the bleed cap 34 causes the distal end 110 of the bleed valve element 92 to move out of recess 102. The rate of bleed is then determined by the cross-sectional area between the cylindrical wall 110 of the bleed valve element 92 and the lumen 100 of the bleed fluid passageway 90.

It is noted that the outer diameter of the cylindrical wall 112 of the bleed valve element 92 may be selected relative to the inner diameter of cylindrical recess 102 to achieve a first bleed rate. Likewise, the inner diameter of the lumen 100 of the bleed fluid passageway 90 may also be selected relative to the outer diameter of cylindrical wall 112 to achieve a second, higher bleed rate. Finally, it is noted that the depth of the cylindrical recess 102 may be selected relative to the pitch of the threads 30 and 42 to determine the amount of counter rotation of the bleed knob 34 required to move the distal end 110 of the bleed valve element 92 out of the cylindrical recess 102. For example, it may be desirous to design the depth of recess 102 relative to the pitch of threads 30 and 42 such that the distal end 110 of the bleed valve element 92 remains in the recess 102 for a quarter to one-half turn of the bleed cap 34. The bleeding then escapes from the bleed fluid passageway 90 via bleed hole 32 formed through the wall 112 thereof.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit of the invention.

Now that the invention has been described, What is claimed is:

1. A flow control valve, comprising in combination:
   a body having a bleed fluid passageway and an axial fluid passageway having an input and output;
   said bleed fluid passageway including a lumen and a bottommost surface, said bottommost surface including a substantially cylindrical recess having a bottom surface and an inner wall defining an inner diameter;
   an output hole positioned in said recess in fluid communication with said axial fluid passageway;
   a bleed hole positioned through said bleed fluid passageway;
   a bleed cap threadably engaging said bleed fluid passageway; and
   a bleed valve element positioned within said bleed fluid passageway, said bleed valve element comprising an elongated configuration having a length appreciably greater than the length of said bleed fluid passageway and a substantially cylindrical distal end having an outer diameter less than said inner diameter, whereby, upon movement of said bleed cap, said distal end moves from its seated engagement with said bottom surface of said recess to a first bleed position within said recess and, upon further movement of said bleed cap, said distal end moves out of said recess to a second bleed position.

2. The flow control valve as set forth in claim 1, wherein said bleed valve element comprises a substantially cylindrical resilient wall.

3. The flow control valve as set forth in claim 1, wherein a lowermost edge of said bleed cap is formed inwardly to prevent said bleed cap from being completely unthreaded from said bleed fluid passageway.

4. The flow control valve as set forth in claim 1, further including check valve means positioned within said input of said axial fluid passageway and oriented to prevent fluid flow from said output to said input of said axial fluid passageway.

5. The flow control valve as set forth in claim 4, wherein said check valve means comprises a check valve having a valve having a element reciprocatingly positioned within a valve housing, said valve element and said valve housing having mating forwardly converging frustro-conical seats which form a fluidtight seal therebetween when fluid back pressure is exerted on said valve element of said check valve.

6. The flow control valve as set forth in claim 1, wherein said bleed fluid passageway and said axial fluid passageway are integrally formed with one another and wherein said substantially cylindrical bleed valve element and said bleed cap are integrally formed with one another.

7. The flow control valve as set forth in claim 6, wherein a plurality of annular barbs are formed on the outside surface of said axial fluid passageway allowing a tube to be connected to said input and said output thereof.

* * * * *